United States Patent [19]

Glover et al.

[11] Patent Number: 4,559,639
[45] Date of Patent: Dec. 17, 1985

[54] X-RAY DETECTOR WITH COMPENSATION FOR HEIGHT-DEPENDENT SENSITIVITY AND METHOD OF USING SAME

[75] Inventors: Gary H. Glover, Waukesha; Edward M. Kerwin, Greendale, both of Wis.

[73] Assignee: General Electric Company, Milwaukee, Wis.

[21] Appl. No.: 443,273

[22] Filed: Nov. 22, 1982

[51] Int. Cl.⁴ .............................................. G03B 41/16
[52] U.S. Cl. ...................................... 378/19; 378/207; 250/367; 250/385
[58] Field of Search ...................... 378/19, 901, 207, 4, 378/16, 159, 145, 14; 250/336.1, 385, 367, 252.1

[56] References Cited

U.S. PATENT DOCUMENTS

| | | | |
|---|---|---|---|
| 3,778,614 | 12/1973 | Hounsfield | 378/7 |
| 3,924,129 | 12/1975 | Le May | 378/901 |
| 3,940,625 | 2/1976 | Hounsfield | 378/901 |
| 4,035,647 | 7/1977 | Hounsfield et al. | 378/19 |
| 4,068,306 | 1/1978 | Chen et al. | 378/901 |
| 4,211,926 | 6/1980 | Nakaya et al. | 250/385 |
| 4,298,799 | 11/1981 | Oliver | 378/4 |
| 4,361,764 | 11/1982 | Zieler | 378/14 |

FOREIGN PATENT DOCUMENTS 372421 3/1923 Fed. Rep. of Germany ...... 378/159

*Primary Examiner*—Craig E. Church
*Assistant Examiner*—Charles F. Wieland
*Attorney, Agent, or Firm*—Alexander M. Gerasimow; Douglas E. Stoner

[57] ABSTRACT

An x-ray detector includes a first array of radiation detecting cells for detecting a planar radiation beam transmitted through an object undergoing examination, and a second array of detector cells for detecting radiation transmitted past the object without substantial attenuation. A cell in the second array is modified so that the fraction of the incident radiation admitted into the cell for detection is dependent on the position of a beam of x-ray radiation on its radiation-receiving aperture. Analysis of the signal outputs of the modified cell and an unmodified cell yields the position of the x-ray beam on the aperture. Knowledge of the beam position is useful in a method for compensating for the height-dependent detector sensitivity in, for example, a computerized tomography apparatus.

27 Claims, 8 Drawing Figures

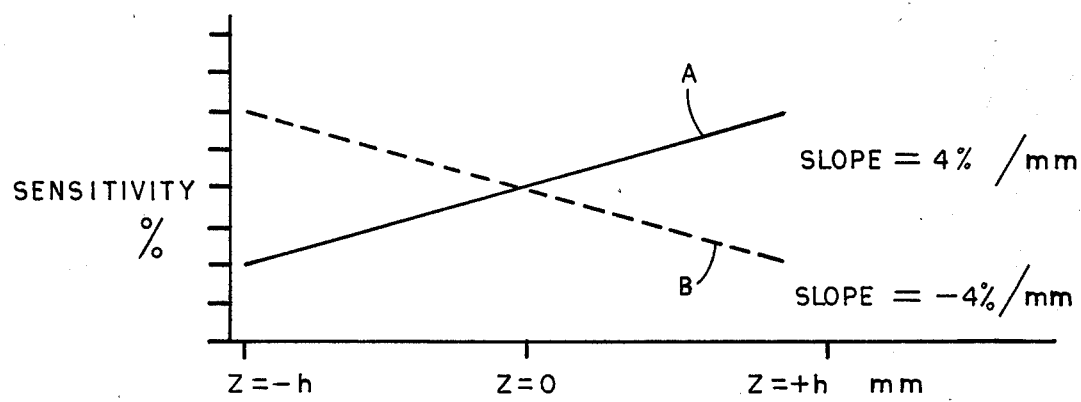
FIG. 3
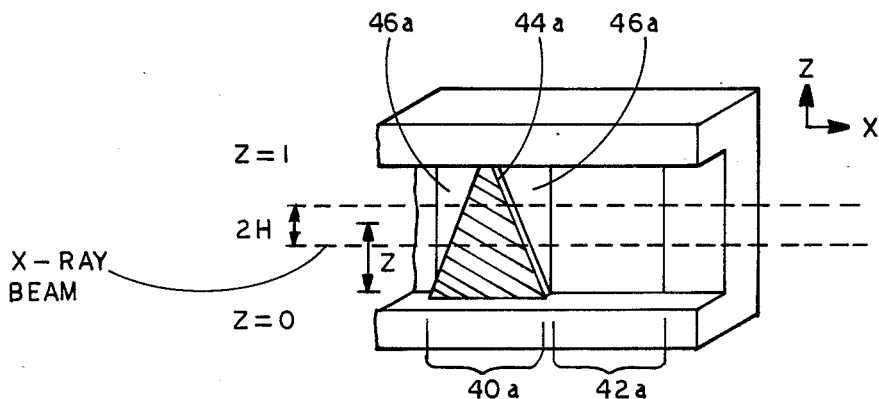
FIG. 4-A
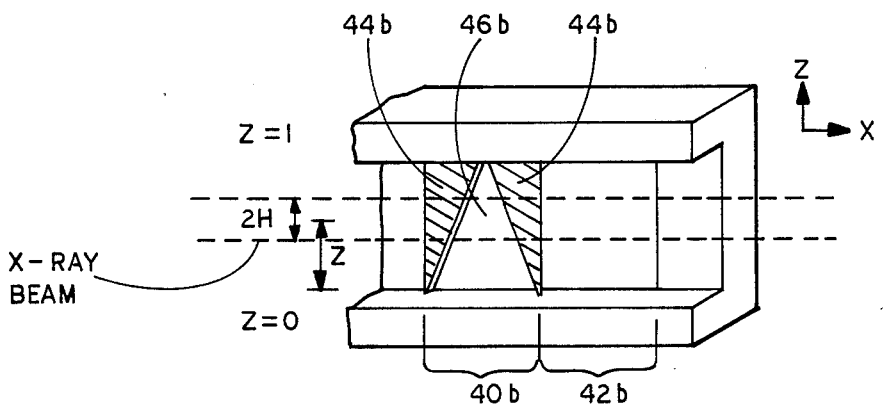
FIG. 4-B

X-RAY DETECTOR WITH COMPENSATION FOR HEIGHT-DEPENDENT SENSITIVITY AND METHOD OF USING SAME

BACKGROUND OF THE INVENTION

This invention relates to multi-channel x-ray detectors of the type used, for example, in computerized tomography imaging systems. More specifically, this invention relates to an improved x-ray detector and a method for using the detector to compensate for the height-dependent sensitivity thereof.

As is known, cross-sectional images of the internal features of an object may be produced by the methods of computerized tomography. In a typical application of those methods, an x-ray source transmits a planar, fan-shaped beam of radiation through the object undergoing examination. Energy transmitted through the object is detected simultaneously in a detector array having, for instance, hundreds of x-ray detector cells. Typically, the position of the x-ray source is changed to irradiate, in the course of imaging, the object from many different intersecting angles. The x-ray detectors function to convert the detected x-ray radiation into electrical signals having magnitudes which are dependent on the intensity of the detected radiation. The electrical signals from each detector cell are amplified and applied along electrical signal paths, commonly referred to as channels, for interpretation in a known way with the aid of a digital computer to produce cross-sectional x-ray images of the internal features of the object.

The xenon gas and the solid-state detectors are among the common detector types used to detect x-rays. In the xenon gas detector, impinging x-ray radiation ionizes xenon gas held under pressure in the detector. The resulting ion-electron pairs are collected on oppositely charged electrode plates. In the solid-state detector, the x-rays excite a scintillator medium to produce optical wavelength radiation which is converted to electrical energy with the aid of photosensors strategically situated in each detector cell. An x-ray detector employing xenon gas is disclosed in U.S. Pat. No. Re. 30,644 assigned to the same assignee as the present invention. U.S. Pat. No. 4,220,860 discloses an x-ray detector which uses a cadmium tungstate scintillator crystal. Both of the aforementioned patents are incorporated herein by reference. It should be noted that, regardless of the type of detector used, the detection of the impinging radiation must be as free of errors as possible. It is necessary, in order to obtain high-quality images, for example, in computerized tomography, that the gain of each detector cell remains stable for the duration of the calibration period. This time period may be several days or weeks.

It has been found by the Applicants herein, however, that detector cell sensitivity is height dependent and accounts for undesirable ring-like features occurring in reconstructed images. That is, Applicants have discovered that detector cell output changes as the position of the x-ray fan beam on the radiation-receiving aperture (window) of the cell changes in a direction orthogonal to the plane of the beam. Such changes in x-ray beam position occur due to thermally induced movement of the focal spot of the x-ray source, therby producing a corresponding movement of the beam in the detector window. Moreover, it has been found that detector cell sensitivity to beam height variations is not identical from cell to cell. As a result, if calibration and actual patient scans are generated at different x-ray tube thermal states, the beam position on the detector windows will be different, and calibration errors will accrue. These errors produce image-degrading errors (artifacts) in the reconstructed images. It is noted that for a typical variation in sensitivity of 0.5%/mm for xenon gas detector cells, a change in the position of the fan beam of only 0.02 mm is sufficient to generate significant ring-shaped artifacts near the center of the image for a rotating detector scan geometry.

The problem could be solved if either the focal spot could be forced to be stationary, or the detector sensitivity could be made uniform. Current state of the art of xenon detectors appears to preclude significant improvement. The height-dependent sensitivity may be even more pronounced with detector arrays using scintillator crystals for which sensitivities of 5%/mm have been measured. Likewise, the thermal stability of high-power (tens of kilowatts) x-ray tubes is not likely to improve significantly.

It is, therefore, an object of the invention to provide an improved detector array having means for measuring the position of an x-ray beam on the aperture of a detector cell, which measurement is useful in compensating for the height-dependent detector sensitivity.

It is another object of the invention to provide a method for compensating for height-and-channel-dependent detector sensitivities so as to reduce image artifacts produced thereby.

SUMMARY OF THE INVENTION

An x-ray detector includes a first plurality of detector cells for detecting a planar beam of radiation transmitted through an object situated between a source of x-rays and the detector cells. Each of the detector cells includes a radiation-receiving aperture having a dimension in a direction orthogonal to the plane of the x-ray beam which exceeds the thickness of the beam measured in the same direction. The detector cells contain an x-ray-detecting medium. The x-ray detector further includes a second plurality of detector cells, substantially identical in nature to the first plurality of cells but fewer in number, for detecting a portion of the x-ray radiation transmitted past the object without substantial attenuation. Means are provided for controllably admitting into at least one of the second plurality of detector cells a predetermined fraction of the total radiation incident thereon in accordance with the position of the x-ray beams on the cell apertures. As a consequence, the output of these cells exhibits a corresponding dependence on the position of the beam. Analysis of the position-dependent signal and the signal from a detector cell detecting substantially all of the unattenuated radiation incident thereon yields the position of the beam on the aperture.

The detector is useful in a method used in conjunction with a computerized tomography apparatus, for example, to compensate for the height-dependent x-ray detector sensitivity. In the method, the sensitivity profile of each of the first plurality of detector cells is determined and a corresponding sensitivity correction factor established based on the position of the x-ray beam on the detector cell aperture. Thereafter, in an actual scan, the position of the x-ray beam on the detector-receiving aperture is measured and used to select a correction factor for each of the first plurality of detector cells. The sensitivity correction factor is used to adjust the gain of the detector cells to compensate for the height-dependent detector sensitivity thereof.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

FIG. 3 illustrates graphically exemplary detector cell sensitivity profiles;

FIG. 4a depicts a preferred embodiment of an x-ray opaque detector cell occluder of the invention;

FIG. 4b depicts another embodiment of an x-ray opaque detector cell occluder of the invention;

DETAILED DESCRIPTION OF THE INVENTION

Figure 1:
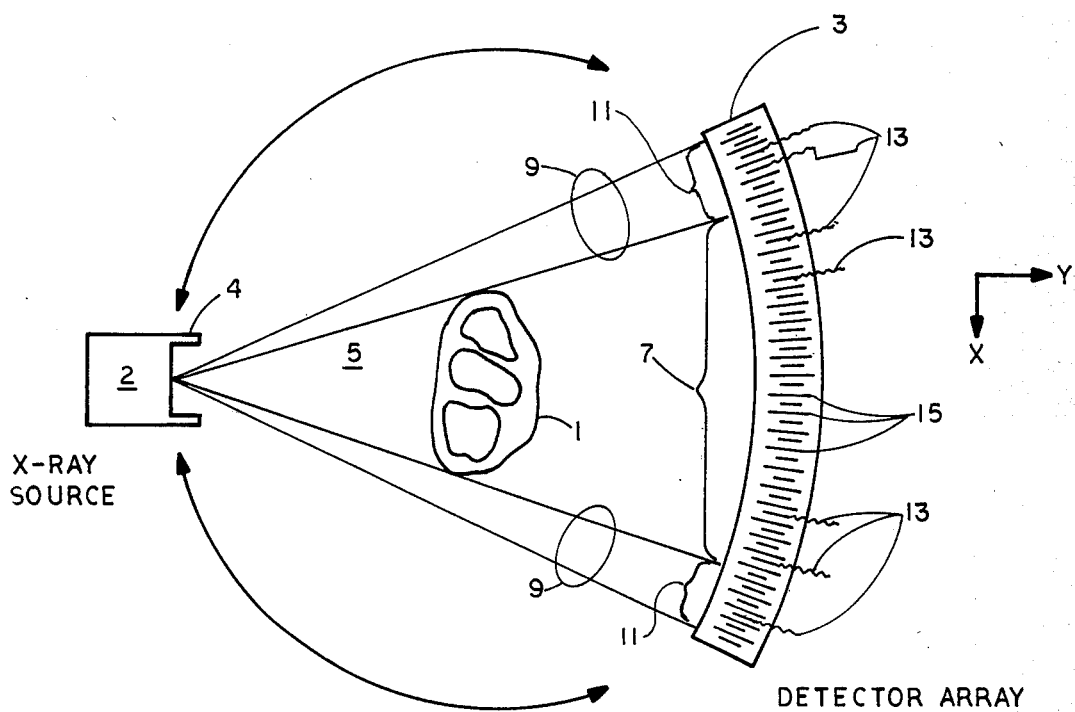
FIG. 1 depicts schematically an x-ray source and x-ray detector array configuration which is useful with the subject invention.

FIG. 1 is a schematic illustration of an x-ray source and detector in a computerized tomography system. A body 1 undergoing examination is interposed between an x-ray source 2 and an array of x-ray detectors 3. In a typical system, the x-ray detector array 3 may, for example, comprise an array of ionization chamber cells filled with xenon gas at a pressure of between approximately 10 atmospheres and approximately 100 atmospheres. X-ray source 2 typically includes a collimation means 4 which functions to confine the x-ray energy emanating from the source into a substantially planar, fan-shaped (sectorial) beam 5. A central sector of x-ray beam 5 irradiates body 1 and is transmitted through the body to a group of ionization chamber cells 7 in the center of array 3. The angle of the x-ray beam is larger than the angle subtended by body 1 so that two peripheral sectors 9 of beam 5 are transmitted past the body without substantial attenuation to two groups of reference ionization chamber cells 11 at the periphery of array 3. In a typical array, central group 7 may, for example, comprise as many as 730 separate ionization chamber cells, while each of the peripheral detector cell groups 11 may comprise a group of six independent ionization chamber cells.

Signals from each detector cell in central group 7 flow into separate data acquisition channels (not shown) for processing by a digital computer (not shown) to produce cross-sectional images of body 1 using techniques well known to the art. Signals from peripheral reference detector cells 11 are also applied to a digital computer for processing. The signals provided by the peripheral detector cells are utilized in a manner more fully described below to compensate the data signals produced by central detector cells 7 for the height-dependent sensitivity of the detector cells. The signals from the reference cells may also be used, for example, to compensate for variations in the intensity of x-ray source 2, as disclosed and claimed in U.S. Pat. Nos. 4,068,306 and 4,070,707, both assigned to the same assignee as the present invention.

Each cell in the array is made up of positively charged anodes 15 and negatively charged cathodes 13. In operation, x-ray photons entering the ionization chamber interact with the xenon gas to produce photoelectron-ion pairs. The positively charged ions are collected at electrodes 13 and induce a signal current therein, while the photoelectrons are collected at anode 15. X-ray cross-talk between adjacent cells is reduced due to the fact that the anodes are constructed from such x-ray opaque materials as either tantalum or tungsten. Thus, the electrical signal obtained at each signal electrode 13 is produced solely by x-ray energy entering a single cell. In order to obtain x-ray attenuation data from many different angles (needed to construct a cross-sectional image), the x-ray source and the detector array are caused, in one embodiment of scan geometries, to rotate jointly either clockwise or counterclockwise about the body, as suggested by the arrows in FIG. 1.

Figure 2:
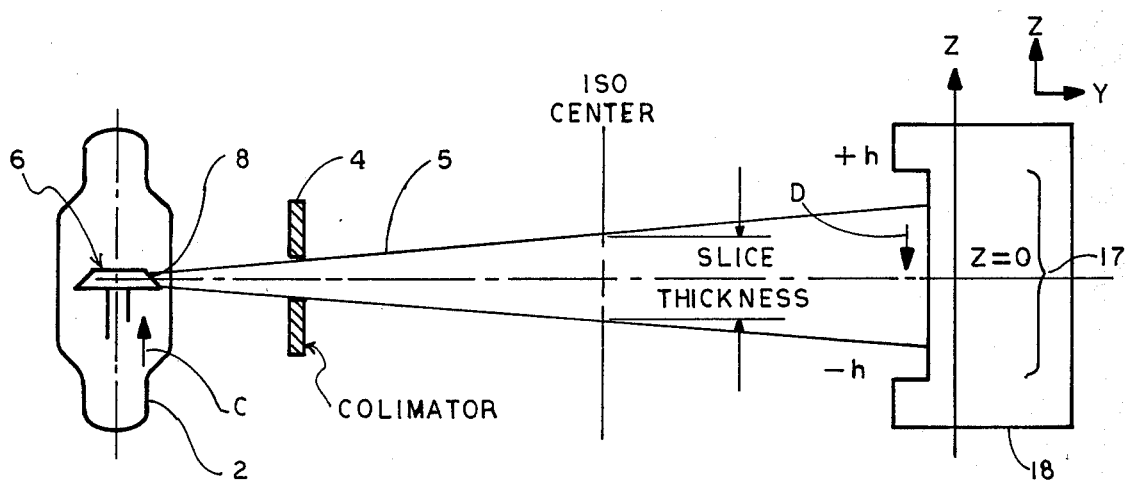
FIG. 2 illustrates schematically x-ray anode drift and the corresponding shift in x-ray beam position at the x-ray detector cell.

Reference is now made to FIG. 2 which depicts schematically a view of the x-ray source and a detector cell drawn prependicular to the scan plane of the fan-shaped beam 5 through one of peripheral reference detector cells 11. The thickness of the fan beam is defined by collimator blades 4 located relatively close to x-ray tube 2 having a rotating anode 6, with a focal spot 8, for generating x-ray energy. Since collimator blades 4 are located near focal spot 8, any axial motion of the anode due to thermal expansion, for example, in the direction of an arrow C shown alongside the shaft of rotating anode 6, will be magnified and manifested as a larger shift in the opposite direction (as indicated by the arrow D) in vertical position (Z) of the beam at a detector window 17 of the detector cell. In a typical system, focal spot motion was found to be of the order of 0.3 mm, while the corresponding motion on the detector window was about 1 mm. As described hereinbefore, a shift in fan-beam position of only 0.02 mm is sufficient to generate objectionable artifacts. It is noted that typical height of detector window 17 is about 25 mm and beam thickness, corresponding to slice thickness at the isocenter (the axis about which the x-ray source and detector rotate), may be between about 2.6 mm and 17 mm.

If detector sensitivity and the body being scanned were uniform in the Z-axis direction, no artifacts would arise. The only effect would be a small shift in the scan plane position through the body. Similarly, if all detector cells were uniformly affected, no artifacts would occur because the reference cells 11 and detector cells 7 (FIG. 1) would be equally affected, and any effects due solely to height-dependent sensitivity would be normalized out by the known reconstruction techniques. It has been found, however, that both the xenon and solid-state detectors exhibit height-dependent cell sensitivities which vary from cell to cell. By way of illustration, the sensitivity profile of one xenon detector cell when scanned from top to bottom was found to vary linearly by 4%/mm. This is graphically illustrated by line A in FIG. 3 which has a slope of about +4%/mm. By way of contrast, another detector cell could have a height-dependent sensitivity profile which is opposite to that depicted at A. This case is illustrated by line B in FIG. 3 having a slope of −4%/mm. The designations $z = -h$, o and $+h$, shown along the horizontal axis of FIG. 3, correspond to bottom, center, and top, respectively, of detector cell window 17 as illustrated in FIG. 2.

It is proposed in accordance with the invention that, if both the position of the beam on a detector window during an actual imaging scan and sensitivity profile of each of detector cells 7 (FIG. 1) were known, then the gain of each detector cell could be corrected by suitable amplification of the electrical output signal. To this end, the sensitivity profile of each detector cell is determined by first performing a scan with no body present (referred to as an air scan) with a cold x-ray tube, and subsequently performing another similar scan with an x-ray tube which has been sufficiently exercised to cause the focal spot to drift. The output of each of detector cells 7 is measured for the cold and hot scans. The sensitivity of the detector has been found to vary substantially linearly between these two points as illustrated by line A in FIG. 3. In this fashion, the sensitivity profile for each detector cell is calculated and stored in the memory of a digital computer, for example, for later use. During scanning, the beam position is again monitored, by one of several means (to be described hereinafter) associated with reference detector cells 11 (FIG. 1), and used to select the appropriate sensitivity correction factor based on the sensitivity profile data previously measured and stored.

The preferred embodiments of an x-ray detector used to determine the position of the x-ray beam at the detector window will now be described with reference to FIGS. 4a and 4b. FIGS. 4a and 4b depict two cell pairs 40a and 42a, and 40b and 42b, respectively, which may be any two of the group of six peripheral reference cells 11 shown at either end of detector array 3 of FIG. 1. Each of cells 40a and 40b, for example, is provided with an x-ray occluder, while cells 42a and 42b are left unobstructed. In the most preferred embodiment shown in FIG. 4a, the occluder assumes the form of a triangular-shaped, x-ray opaque member 44a which may conveniently be formed of aluminum or lead. X-rays enter the detector cell through two remaining openings 46a. Occluder 44b in FIG. 4b is configured to provide a triangular aperture 46b which is formed by two x-ray opaque members 44b. In each embodiment, it is noted that the radiation-admitting apertures have a variable dimension in the Z direction such that the signal output of each occluded cell 40a and 40b, respectively, depends linearly on the position of the x-ray beam (shown by the dashed lines) on the detector cell window. It should be further noted that the triangular configuration of the radiation-receiving apertures is merely exemplary, and any configuration that causes the output of the occluded detector cell to exhibit a dependence (including a non-linear dependence) on the position of the x-ray beam may be used to measure beam position in accordance with the invention.

The manner in which the detector cell embodiments of FIGS. 4a and 4b may be used to measure beam position may be best understood upon consideration of the following analysis. The sensitivity of occluded cells 40a and 40b may be stated as $$S(Z) = aZ, \tag{1}$$

where $0 \leq Z \leq 1$ defines the lower and upper detector aperture limits, as shown in FIGS. 4a and 4b, and $\alpha$ is a constant dependent on the detector and x-ray source. For an x-ray beam having a beam width of 2H and centered at a height Z on the detector face (as shown in FIGS. 4a and 4b), the signal output, $I_Z$, of the occluded detector cells 40a and 40b is given by $$I_Z = \alpha \int_{Z-H}^{Z+H} Z \, dz = 2\alpha H Z. \tag{2}$$

The output, $I_R$, for the unoccluded reference detector cells 42a and 42b is given by $$I_R = \alpha \int_{Z-H}^{Z+H} dz = 2\alpha H. \tag{3}$$

It is apparent from equations (2) and (3) that the height Z of the x-ray beam may be determined by measuring the respective outputs of the occluded and unoccluded detector cells and taking the ratio. Thus, $$\beta = \frac{I_Z}{I_R} = Z, \tag{4}$$

where $\beta$ is defined as the ratio $I_Z/I_R$ and is a measure of beam position Z.

Figure 5:
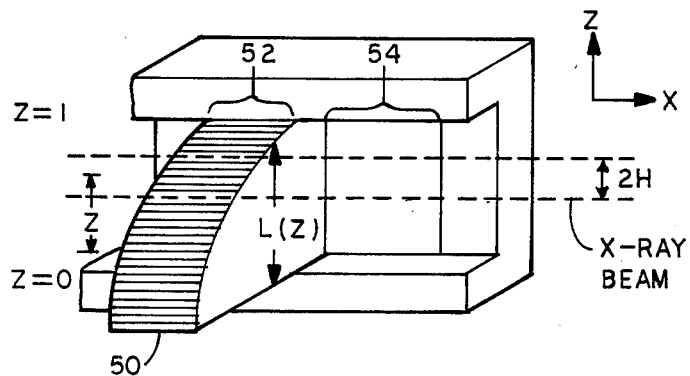
FIG. 5 depicts as yet another embodiment of an x-ray attenuative detector cell occluder in accordance with the invention.

An embodiment of the x-ray detector using an attenuative occluder is depicted in FIG. 5. In this case, an attenuative occluder 50 composed of a material having only moderate effectiveness in blocking x-rays, such as an acrylic plastic, is affixed at the aperture of a reference cell 52. The configuration of attenuative occluder 50 is selected to provide a variable attenuation in the Z-axis direction of the detector cell window. A second unobstructed reference detector cell 54 is also selected. Both cells are part of peripheral cells 11 shown in FIG. 1. The sensitivity, S(Z), of occluded cell 52 (for monoenergetic x-rays) may be expressed as $$S(Z) = \alpha e^{-\mu L(Z)}, \tag{5}$$

in which $\alpha$ is a constant similar to that previously defined, $\mu$ is the x-ray attenuation coefficient of the material of member 50, and $L(Z)$ is a function describing the geometry of the member.

For the same x-ray beam geometry as in FIGS. 4a and 4b, the output of detector cell 52 is given by $$I_Z = \alpha \int_{Z-H}^{Z+H} e^{-\mu L(Z)}, \tag{6}$$

while the sensitivity, $I_R$, of detector cell 54 is given by $2\alpha H$, as in equation (3). The position of the x-ray beam may again be determined by forming the ratio $I_Z/I_R$ such that $$\beta = \frac{I_Z}{I_R} = \frac{1}{2H} \int_{Z-H}^{Z+H} e^{-\mu L(Z)} \, dz. \tag{7}$$

If a particular function L(Z) is selected, such that $\mu L(Z) = \log(1/Z)$, then $$\beta = Z, \text{ as before.}$$

Figure 6:
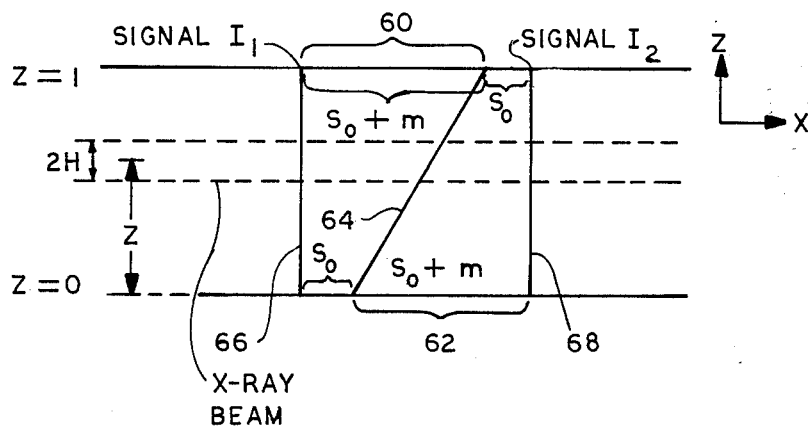
FIG. 6 depicts a further embodiment of a detector cell configuration, having a tilted detector plate, which is useful with the invention.

As yet another embodiment of a detector suitable for determining the position of the x-ray beam is schematically depicted in FIG. 6. This configuration requires an alteration in the cell sidewall geometry of a peripheral detector cell 11 (FIG. 1) in that an anode plate 64 is tilted relative to the adjacent cathode or signal electrodes 66 and 68, for example, such that its slope is m, the shorter detector cell dimension in the X-axis direction is $S_o$, and the longer dimension is given at $S_o+m$, as shown in FIG. 6. The sensitivities of detector cells 60 and 62 are then given by $$S_1 = a(S_o + mZ), \quad (9)$$

and $$S_2 = a[S_o + m(1-Z)], \quad (10)$$

respectively. Hence, for the same x-ray beam configuration as in FIGS. 4a and 4b, the respective outputs $I_1$ and $I_2$ of detector cells 60 and 62 are given by, respectively, $$I_1 = a \int_{Z-H}^{Z+H} (S_o + mZ)dz = a(S_o 2H + m2HZ), \quad (11)$$

and $$I_2 = a \int_{Z-H}^{Z+H} [S_o + m(1-Z)]dz = [(S_o + m)2H - m2HZ]. \quad (12)$$

Then, $\beta$ is defined as $$\beta = \frac{I_1 - I_2}{I_1 + I_2} = \frac{\frac{M}{2}\left(Z - \frac{1}{2}\right)}{2S_o + m}, \quad (13)$$

which is again a measure of Z.

While the description of the embodiment depicted in FIG. 6 refers, for definition, to a xenon gas detector, it should be realized that the same performance can be achieved with solid-state detectors having scintillator crystal bars shaped, for example, to have radiation-receiving apertures similar to those of detector cells 60 and 62. It is to be noted that adjacent detector cells in the scintillation detector need not be separated by metallic, x-ray-opaque collimator plates. Conveniently, cross talk may be reduced by application of an x-ray-opaque coating, for example, to the lateral surfaces of scintillator crystals.

Figure 7:
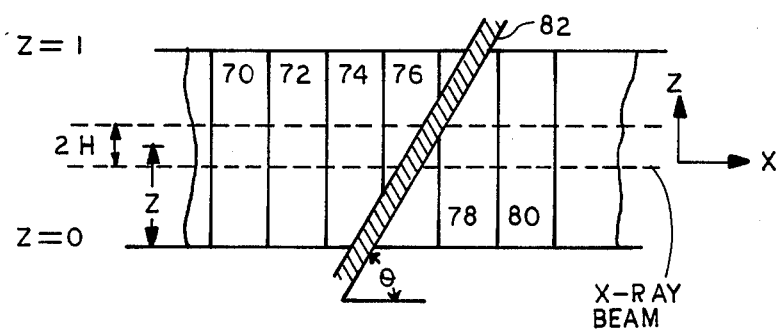
FIG. 7 depicts another inventive detector cell configuration, including an x-ray-opaque, wire-like member positioned at an angle relative to the plane of the x-ray beam.

FIG. 7 depicts still another detector array configuration useful in measuring the position of the x-ray beam in the Z direction. In this embodiment, an elongated x-ray opaque member 82, such as a wire, is positioned at an angle $\theta$ relative to the plane of the beam across several detector cells 74-78, for example, forming part of peripheral cells 11 of FIG. 1. The position of the x-ray "shadow" across the detector cells produced under x-ray beam irradiation changes in the horizontal direction (X-direction) depending on the position Z of the x-ray beam. If the beam is near the upper detector boundary (Z=1) of the detectors, for example, then its shadow will be detected by the reduced signal output from detector cell 78, relative to the output of an unoccluded cell such as 80. As the position of the beam moves downward, it is apparent that the shadow will move horizontally toward detector cell 76 where it will be detected again by the decrease in signal output. By monitoring the relative outputs of the detector cells, the position of the beam may be determined, as $\Delta Z = \Delta X \tan \theta$.

A method by which the Z-position of an x-ray beam, determined using one of the detector configurations disclosed above, may be used to compensate for the height-dependent detector sensitivity will be described next.

A first step in this process is to determine the sensitivity profile for each of the group of detector cells 7 (FIG. 1) which detect the imaging radiation transmitted by body 1. This is accomplished in the manner described hereinbefore by performing a first air scan (i.e., without the presence of body 1) with a cold x-ray tube and then performing a second air scan with an x-ray tube which has been exercised to produce a substantial shift in the position of the beam. If it is not desired to make a linear approximation, measurements may be taken at intermediate points. Following each scan, the output of each of the detector cells is measured and stored for later use. For each of the scans, the position of the x-ray beam on the detector cell is also recorded. This calibration procedure need be performed only once upon installation of a new x-ray tube, for example, or upon the occurrence of some other event affecting the x-ray tube—detector positional configuration.

Thereafter, in performing actual imaging, it is merely necessary to determine the position of the x-ray beam for each scan. The beam position will typically be somewhere between the "cold" and "hot" calibration scans, and since the detector cell sensitivity has been found to be substantially linear (see plot A, FIG. 3), the correct compensation factor may be found by interpolation. For example, if the sensitivity of a given detector cell has been found to vary by 4%/mm, and if the beam position for a given scan is measured and found to have changed by 2 mm from what had previously been measured for the "cold" calibration reference point, then the sensitivity of that detector cell has increased by 8% (4%/mm × 2 mm) over that which had been measured for the "cold" calibration scan. It should be noted that, if another detector cell is found to have a sensitivity profile such as that shown by line B (FIG. 3) having a negative slope of 4%/mm, then for the same beam displacement of 2 mm the sensitivity of this detector cell would have decreased by 8%. Thus, for these two detector cells the level of the signal detected in an actual scan would be increased and decreased 8%, respectively, to compensate for the change in sensitivity due to the change in the position of the beam. The output signal levels of each of the detector cells in group 7 is adjusted in a similar manner.

It should be noted that the detector embodiments for detecting the position of the x-ray beam described above may be used advantageously with x-ray detector arrays using either xenon gas or scintillator crystal detectors and in apparatus other than computerized tomography scanners. Additionally, although the preferred position for the reference detector cells 11 used for the calibration and detection of the position of the beam is at the periphery of the detector array 3 (FIG. 1), other intermediate positions to the x-ray source and the detector array, such as at the collimator, may also be effectively employed.

The inventive x-ray detector and method for compensating for height-dependent detector cell sensitivity may be used with the computed projection radiography method which employs the same apparatus as computerized tomography. In the computed projection radiography method, the x-ray source and detector are held in a fixed position rather than being orbited to scan the object from many different angles as in computerized tomography. In this method, the patient must be advanced through the fan-shaped x-ray beam at a very constant velocity for undergoing a line-by-line scan with a fan beam that is about 1.5 mm thick, for example. As the patient is being advanced, the x-ray detector cells yield signals corresponding to x-ray attenuation at closely successive positions of the patient on a line-by-line basis, and the resulting attenuation data is stored until the length of the body which is of interest has been scanned. A computer then uses the attenuation data to produce digital data representative of the intensities of the picture elements for all scan lines, and these signals are used to drive a video monitor which displays a visual image corresponding to the projected x-ray image. In effect, the computed projection radiography method yields a visual x-ray image that is comparable to the image obtained with ordinary radiographic film but with greater contrast than is obtainable with film because the dynamic range of the x-ray detector is usually greater than that of film.

From the foregoing, it will be appreciated that in accordance with the invention there is provided an improved detector array having means for measuring the position of an x-ray beam on the aperture of a detector cell and which may be used to obtain the sensitivity profiles of the detector cells comprising the detector array. Additionally, a method is provided for compensating for the height-dependent detector sensitivity using the sensitivity profiles and beam position obtained with the improved detector array.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. An x-ray imaging apparatus, comprising:
    (a) an x-ray source providing a substantially planar beam of x-ray energy;
    (b) an x-ray detector positioned in a spaced-apart relationship from said x-ray source such that an object to be studied may be accomodated therebetween, said x-ray detector having:
        (1) a first plurality of detector cells substantially coplanar with said x-ray beam, each of said detector cells including a radiation-receiving aperture having a dimension in a direction orthogonal to the plane of said beam exceeding the thickness of said beam measured in the same direction, said plurality of detector cells containing an x-ray-detecting medium and being disposed for detecting x-ray radiation transmitted through said object;
        (2) a second plurality of x-ray detector cells, substantially identical to said first plurality of cells, for detecting a portion of said x-ray radiation beam transmitted past said object without substantial attenuation; and
    (c) an x-ray attenuative member fixedly disposed between said x-ray source and at least one, but not all, of said second plurality of detector cells, said x-ray member having a variable x-ray transmissive capability in a direction substantially perpendicular to the plane of said x-ray beam for controllably admitting into said one detector cell a predetermined fraction of the total radiation incident thereon in accordance with the position of said x-ray beam on the radiation-receiving aperture of said one cell, as a consequence of which the output thereof exhibits a corresponding dependence on the position of said x-ray beam.

2. The x-ray imaging apparatus of claim 1 wherein said x-ray attenuative member comprises an x-ray opaque member having an opening formed therein for admitting radiation into said one detector cell, said opening being configured such that the fraction of radiation admitted thereinto is dependent on the position of said beam on the radiation-receiving aperture of said one cell.

3. The x-ray imaging apparatus of claim 2 wherein the opening formed in said opaque member is configured such that the fraction of radiation admitted into said one detector cell exhibits a linear dependence on the position of said x-ray beam on the radiation-receiving aperture thereof.

4. The x-ray imaging apparatus of claim 3 wherein said member comprises a member having a triangular opening formed therein.

5. The x-ray imaging apparatus of claim 4 wherein said member comprises an x-ray opaque material selected from the group consisting of aluminum and lead.

6. The x-ray imaging apparatus of claim 2 wherein said member is disposed at the radiation-admitting aperture of said one detector cell.

7. The x-ray imaging apparatus of claim 2 wherein said x-ray source further comprises collimator means for producing said planar x-ray beam, and wherein said second plurality of detector cells is disposed adjacent to said collimator means.

8. The x-ray imaging apparatus of claim 1 wherein said x-ray attenuated member comprises an attenuative occluder disposed between said x-ray source and one of the detector cells forming part of said second plurality of detector cells, said occluder configured to have an x-ray transmissivity which varies in a direction orthogonal to the plane of said x-ray beam such that a predetermined fraction of the total radiation incident upon said one detector cell is admitted thereinto in accordance with the position of said x-ray beam on the radiation-receiving aperture thereof.

9. The x-ray imaging apparatus of claim 8 wherein said attenuative occluder is disposed at the radiation-admitting aperture of said one detector cell.

10. The x-ray imaging apparatus of claim 8 wherein said attenuative occluder comprises an acrylic-plastic material.

11. The x-ray imaging apparatus of claim 8 wherein said x-ray source comprises collimator means for producing said planar x-ray beam, and wherein said second plurality of detector cells is disposed adjacent to said collimator means.

12. The x-ray imaging apparatus of claim 1 wherein said x-ray-detecting medium comprises xenon gas and wherein said first and second plurality of detector cells comprise electrically conductive, oppositely charged electrodes.

13. The x-ray imaging apparatus of claim 1 wherein said x-ray-detecting medium comprises a scintillator material.

14. The x-ray imaging apparatus of claim 1 wherein said x-ray attenuative member comprises an x-ray-opaque, elongated member disposed between said x-ray source and said second plurality of detector cells, said elongated member being tilted at a predetermined angle relative to the plane of said x-ray beam so as to partially occlude predetermined ones of said second plurality of cells such that one of said occluded detector cells, depending on the position of said x-ray beam on the radiation-receiving aperture thereof, receives less x-ray radiation than unoccluded ones of said second plurality of cells.

15. The x-ray imaging apparatus of claim 1 wherein said x-ray source comprises collimator means for producing said planar x-ray beam, and wherein said second plurality of detector cells is disposed adjacent to said collimator means.

16. A method for compensating for height-dependent sensitivity of an x-ray detector useful in apparatus of the type including an x-ray source having an anode and producing a planar beam of x-ray radiation, and wherein said x-ray detector includes a first plurality of detector cells for detecting radiation transmitted through an object disposed between said source and said detector, and a second plurality of detector cells for detecting x-ray radiation transmitted past said object without substantial attenuation, said detector cells having a radiation-receiving aperture with a dimension in a direction orthogonal to the plane of said beam exceeding the thickness of said beam measured in the same direction, said method comprising the steps of:
(a) determining the sensitivity profile of each of said first plurality of detector cells;
(b) calculating a plurality of sensitivity correction factors for each of said first plurality of detector cells, said correction factors being dependent on the position of said x-ray beam on the radiation-receiving aperture of said detector cells;
(c) measuring the position of said x-ray beam on the x-ray detector cell radiation-receiving aperture while scanning said object with said x-ray beam;
(d) selecting a sensitivity-correction factor for each of said first plurality of detector cells in accordance with the measured position of said x-ray beam; and
(e) adjusting the output level of each of said first plurality of detector cells based on the selected sensitivity-correction factor.

17. The method of claim 16 wherein said step (a) comprises the steps of:
(f) measuring the output of each of said first plurality of detector cells while performing an air scan with said x-ray source in a cold state;
(g) exercising said x-ray source sufficiently to achieve substantial displacement of said anode due to thermal expansion, resulting in a corresponding displacement of said x-ray beam on the radiation-receiving aperture; and
(h) repeating said step (f) for the displaced position of said x-ray beam.

18. The method of claim 16 wherein said step (c) comprises the step of:
positioning an x-ray opaque member between said x-ray source and at least one detector cell forming part of said second plurality of detector cells, said member having an opening formed therein for admitting radiation into said one detector cell, said opening being configured such that the fraction of the radiation admitted thereinto is dependent on the position of said beam on the radiation-receiving aperture of said one cell wherein the output thereof exhibits a dependence on the position of said x-ray beam.

19. The method of claim 18 wherein the opening formed in said opaque member is configured such that the fraction of radiation admitted into said detector cell exhibits a linear dependence on the position of said x-ray beam in the radiation-receiving aperture thereof.

20. The method of claim 19 wherein said step (c) further comprises the step of:
forming the ratio, $\beta$, of the output of said occluded cell and the output of an unoccluded detector cell forming part of said second plurality of detector cells, such that $$\beta = Z,$$

where $Z$ is a measure of the position of said x-ray beam on the radiation-receiving aperture of said detector cell.

21. The method of claim 19 wherein said member comprises a member having a triangular opening formed therein.

22. The method of claim 18 wherein said member is disposed at the radiation-receiving aperture of said one detector cell.

23. The method of claim 16 wherein said step (c) comprises the step of:
positioning an attenuative occluder between said x-ray source and at least one of the detector cells forming part of said second plurality of detector cells, said occluder configured to have an x-ray transmissivity which varies in a direction orthogonal to the plane of said x-ray beam, such that a predetermined fraction of the total radiation incident upon said one detector cell is admitted thereinto in accordance with the position of said x-ray beam on the radiation-receiving aperture thereof, and wherein the output thereof exhibits a dependence on the position of said x-ray beam.

24. The method of claim 16 wherein said step (c) comprises the step of:
providing each of a pair of detector cells forming part of said second plurality of detector cells with radiation-receiving apertures, such that the radiation-receiving aperture of a first one of said pair of detector cells decreases, while the aperture of a second one of said pair of detector cells increases correspondingly in a direction orthogonal to the plane of said x-ray beam.

25. The method of claim 24 wherein the radiation-receiving aperture of each of said pair of cells is configured such that the fraction of the radiation admitted thereinto exhibits a linear dependence on the position of said x-ray beam on the aperture.

26. The method of claim 25 wherein said step (c) further comprises the step of:
forming the quotient, $\beta$, of the difference in the respective outputs of said pair of detector cells and the sum of the outputs thereof such that $$\beta = \frac{\frac{M}{2}\left(Z - \frac{1}{2}\right)}{2S_o + m},$$

where:
m is the slope of said tilted side-wall member,
$S_o + m$ is the maximum width of each of said pair of detector cells coplanar with said x-ray beam, and
Z is the position of said x-ray beam on the radiation-receiving aperture of said pair of detector cells.

27. The method of claim 16 wherein said step (c) comprises the step of:
providing an x-ray-opaque, elongated member between said x-ray source and said second plurality of detector cells, said member being tilted at a predetermined angle relative to the plane of said beam so as to partially occlude predetermined ones of said second plurality of cells such that one of said occluded detector cells, depending on the position of said x-ray beam on the radiation-receiving aperture thereof, receives less x-ray radiation than unoccluded ones of said second plurality of cells.

* * * * *